(12) United States Patent
Kwon et al.

(10) Patent No.: US 12,016,982 B2
(45) Date of Patent: Jun. 25, 2024

(54) FILTER AND FILTERING SYSTEM INCLUDING THE SAME

(71) Applicant: Samsung Electronics Co., Ltd., Suwon-si (KR)

(72) Inventors: Hyukjae Kwon, Suwon-si (KR); Minseok Koo, Suwon-si (KR); Hyun Chul Lee, Hwaseong-si (KR); Sukeun Kuk, Suwon-si (KR); Dongsik Yang, Seoul (KR); Sehyeong Oh, Seoul (KR); Inhyuock Cho, Yongin-si (KR); Sangmin Ji, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 460 days.

(21) Appl. No.: 17/370,357

(22) Filed: Jul. 8, 2021

(65) Prior Publication Data
US 2022/0280674 A1    Sep. 8, 2022

(30) Foreign Application Priority Data

Mar. 4, 2021    (KR) .................. 10-2021-0029055

(51) Int. Cl.
*A61L 9/18* (2006.01)
*A61L 9/20* (2006.01)
(Continued)

(52) U.S. Cl.
CPC ............ *A61L 9/18* (2013.01); *B01D 46/0002* (2013.01); *B01D 46/0028* (2013.01); *B01D 53/007* (2013.01); *B01D 53/8668* (2013.01); *A61L 2101/26* (2020.08); *A61L 2209/14* (2013.01); *B01D 2255/20707* (2013.01); *B01D 2255/20776* (2013.01); *B01D 2255/802* (2013.01); *B01D 2257/708* (2013.01); *B01D 2259/804* (2013.01); *B01D 2279/65* (2013.01)

(58) Field of Classification Search
CPC ..................................... A61L 9/18; A61L 9/20
See application file for complete search history.

(56) References Cited

U.S. PATENT DOCUMENTS

2009/0010801 A1 * 1/2009 Murphy ................ B01D 46/10
                                                            422/4
2021/0094026 A1    4/2021 Kwon et al.

FOREIGN PATENT DOCUMENTS

JP    2002191682 A  *  7/2002
JP    2002238981 A  *  8/2002
(Continued)

OTHER PUBLICATIONS

English Translation of Japanese Document No. JP 2002191682A provided by the USPTO: Shiga, Azusa; Air Cleaner and Air Cleaning Filter; Jul. 9, 2002 (Year: 2002).*

(Continued)

*Primary Examiner* — Kevin Joyner
(74) *Attorney, Agent, or Firm* — CANTOR COLBURN LLP (57) ABSTRACT

A filter and a filter system including the filter. The filter includes a porous filter frame having a first upstream-side surface, and a second downstream-side surface based on a thickness direction, the porous filter frame filtering particulate matter. A copper material layer is disposed on at least a portion of the first upstream-side surface of the filter frame.

18 Claims, 9 Drawing Sheets

(51) Int. Cl.
  *B01D 46/00* (2022.01)
  *B01D 53/00* (2006.01)
  *B01D 53/86* (2006.01)
  *A61L 101/26* (2006.01)

(56) References Cited

FOREIGN PATENT DOCUMENTS

| KR | 10-1832849 B1 | 2/2018 |
| KR | 10-1925846 B1 | 12/2018 |
| KR | 10-1992650 B1 | 6/2019 |
| KR | 10-20200014494 A | 2/2020 |
| KR | 10-20200032387 A | 3/2020 |
| KR | 10-20210039201 | 4/2021 |

OTHER PUBLICATIONS

English Translation of Japanese Document No. JP 2002238981A provided by the European Patent Office website espacenet.com: Air Cleaning Device; Aug. 27, 2002 (Year: 2002).*
English Abstract of KR 10-1925846.
English Abstract of KR 10-2017-0063088 for KR 10-1832849.
English Abstract of KR10-2020-0014494.
English Abstract of KR10-2020-0032387.
English Abstract of KR20190068029 for KR 10-1992650.

* cited by examiner

FILTER AND FILTERING SYSTEM INCLUDING THE SAME

CROSS-REFERENCE TO RELATED APPLICATION

This application claims priority under 35 U.S.C. § 119 to Korean Patent Application No. 10-2021-0029055, filed on Mar. 4, 2021, in the Korean Intellectual Property Office, the content of which is incorporated by reference herein in its entirety.

BACKGROUND

1. Field

The present disclosure relates to a filter and a filter system including the filter.

2. Description of the Related Art

To reduce fine dust, filters woven with melt blown, glass fiber, or plastic, or filters in a nonwoven state are used. Such filters are classified as a medium class, HEPA class, and ULPA class according to use. In the case of removing volatile organic compounds (VOC) including fine dust, the VOC is filtered by a deodorizing filter that adsorbs (deodorizes) the VOC by using carbonates such as activated carbon. These filters are currently applied in air purifiers, heat exchange ventilators, or air conditioning filters. In recent years, a filter that may remove biomaterials such as viruses and bacteria is also of interest.

SUMMARY

Provided is a filter capable of removing particulate matter, gas gaseous materials, and biomaterials.

Provided are filter systems including such a filter.

Additional aspects will be set forth in part in the description which follows and, in part, will be apparent from the description, or may be learned by practice of the presented embodiments.

According to an aspect of an embodiment, a filter includes: a porous filter frame having a first upstream-side surface and a second downstream-side surface based on a thickness direction, the porous filter frame filtering particulate matter; and a copper material layer disposed on at least a portion of the first upstream-side surface.

The copper material layer may include copper(0), copper (I), or a combination thereof.

The filter may further include a photocatalyst layer that is disposed on the second downstream-side surface, and the photocatalyst layer is activated by light energy.

The photocatalyst layer may include a metal compound that has a semiconductor characteristic in response to light exposure, and the metal compound may include $TiO_2$, $WO_3$, or a combination thereof.

The filter frame may include a catalyst material that is activated by energy other than light to remove a gaseous materials.

The filter frame may include a photocatalyst material activated by light energy.

The filter frame may include a plurality of first channels extending in a thickness direction in which particulate matter enters and flows within the filter frame, and having an open upstream-side and a closed downstream side, and a plurality of second channels extending in the thickness direction and having an open downstream-side and a closed upstream side, and the plurality of first channels and the plurality of second channels are alternately arranged in a two-dimensional arrangement in a plane orthogonal to the thickness direction.

The filter frame may include a first portion that closes the downstream-side of the first channel, a second portion that closes the upstream-side of the second channel, and a third portion disposed between the first channel and the second channel.

The copper material layer may be disposed on a first surface of the third portion.

The copper material layer may be disposed on a first surface of the second portion and a first surface of the third portion. The filter may further include a photocatalytic layer disposed on a second surface of the third portion, and is activated by light energy.

The photocatalyst layer may be formed on a second surface of the first portion and a second surface of the third portion.

The filter frame may include a catalyst material that is activated by energy other than light energy to remove gaseous materials.

The filter frame may include a photocatalyst material that is activated by light energy.

According to an aspect of an embodiment, a filter system includes: a porous filter frame having a first upstream-side surface, and a second downstream-side surface based on a thickness direction, the porous filter frame filtering particulate; and a copper material layer disposed on at least a portion of the first surface; and a light source configured to irradiate the second downstream-side surface of the filter frame.

The filter system may further include a photocatalytic layer that is disposed on the second downstream-side surface, and is activated by light energy that irradiates from the light source.

The filter frame may include a catalyst material that is activated by energy other than light to remove a gaseous materials.

The filter frame may include a photocatalyst material that is activated by light energy irradiated from the light source.

The filter frame may include a plurality of first channels extending in a first direction and having an open upstream-side and a closed downstream-side, and a plurality of second channels extending in the first direction and having an open downstream-side and a closed upstream side, and the plurality of first channels and the plurality of second channels may be alternately arranged in a two-dimensional arrangement in a plane orthogonal to the first direction.

The filter frame may include a first portion that closes the downstream-side of the first channel, a second portion that closes the upstream-side of the second channel, and a third portion disposed between the first channel and the second channel, and the copper material layer may be disposed on a first surface of the third portion.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, a filter and a filter system employing the filter according to an embodiment will be described in detail with reference to the accompanying drawings. In the drawings, thicknesses of layers or regions may be somewhat exaggerated for clarity of the specification. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. In addition, when a material disposed on "at least a portion" of a surface, the material may be disposed on all or a portion of the surface.

Filters illustrated herein may be one of many means for purifying air. Further, filters shown herewith may be one of many means for filtering or removing substances from air that may be harmful or harmful to human breathing. Filters shown herein may be one of many means for discharging a relatively cleaner fluid than the fluid that enters the filter, e.g., through an inlet side of the filter.

Figure 1:
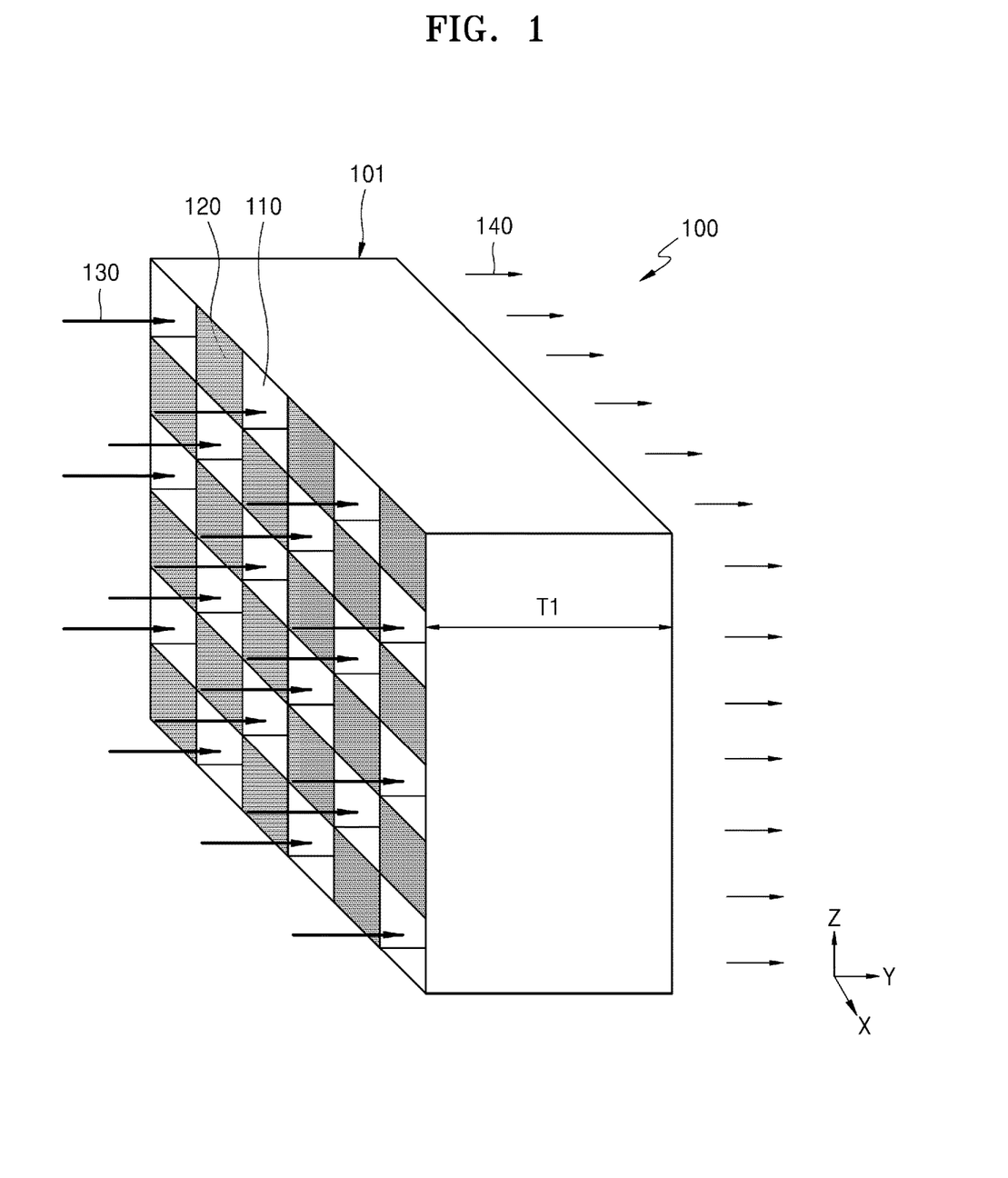
FIG. 1 is a perspective view of a filter according to an embodiment.
Figure 2:
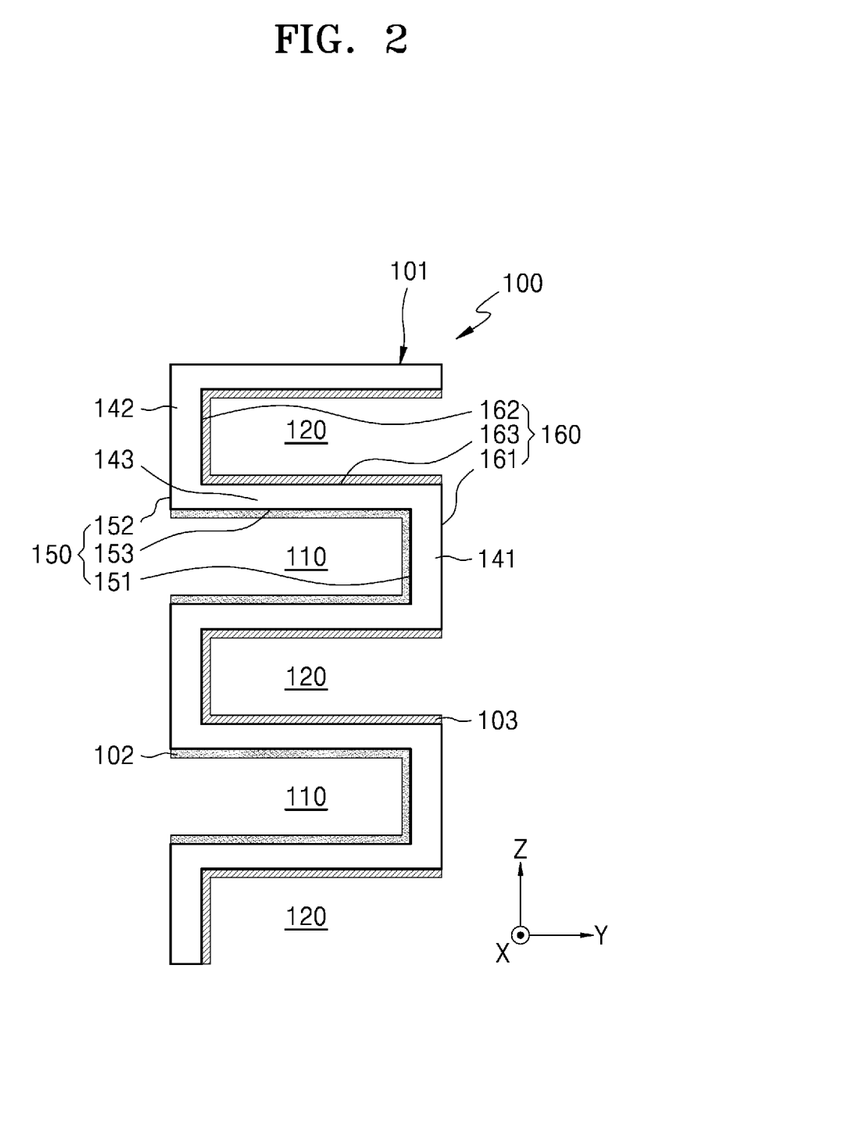
FIG. 2 is a cross-sectional view of the filter shown in FIG. 1.

FIG. 1 is a perspective view of a filter 100 according to an embodiment. FIG. 2 is a cross-sectional view of the filter 100 shown in FIG. 1. Referring to FIGS. 1 and 2, the filter 100 may include a filter frame 101, and a copper material layer 102. The filter 100 may further include a photocatalyst layer 103. The filter frame 101 includes an inlet surface (a first surface) 150 through which a gas including a material to be removed or degraded may enter the filter 100. For example, a material 130 flows into the filter 100 and a purified gas stream 140, e.g., air, is discharged from a second surface a plane 160. The copper material layer 102 is disposed on at least a portion of the first surface 150. The photocatalyst layer 103 is disposed on at least a portion of the second surface 160. As an example, the material 130 may include particulate matter, such as fine dust, biomaterials, such as virus or bacteria, and gaseous materials, such as volatile organic compounds. The filter frame 101 has a structure capable of filtering particulate matter. For example, the filter frame 101 has a porous structure capable of filtering particulate matter.

The filter frame 101 may have a thickness T1. The first surface 150 and the second surface 160 are opposite each other in the thickness direction T1, for example, in a Y-direction. The thickness direction (Y) is a flow direction of the material 130 within the filter frame.

The filter frame 101 has a wall-flow structure. For example, the filter frame 101 may include a plurality of first channels (or cells or grooves) 110 and a plurality of second channels (or cells or grooves) 120. The plurality of first channels 110 extend in the thickness direction Y and have an open upstream-side and a closed downstream-side. The plurality of second channels 120 extend in the thickness direction Y and have an opened downstream-side and a closed upstream side. The material 130 enters the filter frame 101 through the plurality of first channels 110, and the gas passing through the filter frame 101 is discharged through the plurality of second channels 120. A gas discharged through the plurality of second channels 120 may be a relatively clean or harmless gas, or may include gas and air as a result of filtering out of harmful substances or impurities from the material 130 introduced to the filter 100 through the first channel 110.

The plurality of first channels 110 and the plurality of second channels 120 may be regularly or irregularly arranged. For example, the plurality of first channels 110 and the plurality of second channels 120 may be alternately arranged in a two-dimensional arrangement in a plane orthogonal to the thickness direction Y, for example, in a plane defined by the X-direction and Z-direction. The filter frame 101 may have a shape in which the plurality of first channels 110 and the plurality of second channels 120 are defined. For example, the filter frame 101 may include a first portion 141 for closing a downstream-side of the first channel 110, and a second portion 142 for closing an upstream-side of the second channel 120, and a third portion 143 disposed between the first channel 110 and the second channel 120. As used herein, "closing" includes all manner of restricting access, including blocking. The first portion 141 and the second portion 142 are separated from each other in the thickness direction Y, and a plurality of first portions 141 and a plurality of second portions 142 are arranged in the Z-direction. The third portion 143 may be connected to the second portion 142 by extending from an edge of the first portion 141 in the Y-direction. The plurality of first portions 141 and the plurality of second portions 142 are connected in a zigzag shape in the Z-direction and the X-direction by the plurality of third portions 143. The thickness of the first portion 141 and the second portion 142 may be the same as or different from the thickness of the third portion 143. The upstream-side surfaces 151, 152, 153 of the first portion 141, the second portion 142, and the third portion 143 become the first surface 150, and the downstream-side surfaces 161, 162, and 163 of the first portion 141, the second portion 142, and the third portion 143 become the second surface 160. Accordingly, the filter frame 101 having a wall-flow structure in which areas of the first surface 150 and the second surface 160 are expanded may be implemented.

The sizes of the first channel 110 and the second channel 120 may be the same or different. For example, a width in the X-direction and a width in the Z-direction of the first channel 110 may be the same as or different from a width in the X direction and a width in the Z-direction of the second channel 120, respectively. A length of the first channel 110 in the thickness direction Y may be the same as or different from a length of the second channel 120 in the thickness direction Y. The sizes of the plurality of first channels 110 may be the same or may be different. The sizes of the plurality of second channels 120 may be the same or different.

The filter frame 101 may be a single body in which the first portion 141, the second portion 142, and the third portion 143 are connected as one body. The filter frame 101 may include a porous material, for example, a porous ceramic material capable of filtering particulate matter. The ceramic material may include, for example, cordierite, SiC, $Al_2TiO_5$, and the like. The permeability of the first portion 141 and the second portion 142 may be lower than that of the third portion 143. In this case, the material 130 flows into the filter frame 101 through the first channel 110, and a gas mainly passes through the third portion 143 and is discharged through the second channel 120. Of course, the first portion 141 and the second portion 142 may be non-permeable portions.

The copper material layer 102 may be provided in at least a portion of the first surface 150 of the filter frame 101. Without being bound by theory, it is believed that the copper material layer 102 removes viruses, bacteria, etc. by an oligodynamic action. Copper ions on a surface of the copper material layer 102 are adsorbed onto or absorbed into viruses or bacteria. The adsorbed or absorbed copper ions make holes in or otherwise disrupt the cell membrane of the viruses or bacteria, thereby resulting in the loss of nutrients and moisture from the viruses or bacteria, and allowing or attracting activated oxygen to enter through the pores or disruptions formed in the cell membrane. The DNA and protein of viruses and bacterial are damaged and modified by the activated oxygen, and thus, the viruses and bacteria are killed or weakened. The copper material layer 102 may include Cu, Cu oxide, Cu glass, and the like. The copper material layer 102 may include copper(0) or copper(1) each exhibiting a strong oligodynamic action. The 0-valent copper may include, for example, Cu. The copper(I) may include, for example, $Cu_2O$. The copper material layer 102 may be disposed on at least a portion of the first surface 150 of the filter frame 101 by coating, chemical vapor deposition, physical vapor deposition, etc. The copper material layer 102 may be in a form through which particulate matter may pass. For example, the copper material layer 102 may have a form in which copper material wires are intertwined, a copper material powder form, a copper material rod form, a copper material nonwoven form, a copper material mesh form, or the like.

The material 130 mainly flows into the filter frame 101 through the first channel 110, particulate matter in the material 130 are filtered by the third portion 143, and a gas passed through the third portion 143 is discharged through the second channel 120. The copper material layer 102 may be disposed on the upstream-side surface 153 of at least the third portion 143 of the first surface 150. Bio-particles, such as viruses or bacteria in the material 130 contact the copper material layer 102 provided on the upstream-side surface 153 of the third portion 143 and are rendered harmless (or killed) by an oligodynamic effect. Because the material 130 flows in the thickness direction Y, the material 130 introduced into the first channel 110 collides with the upstream-side surface 151 of the first portion 141. Considering this point, the copper material layer 102 may be formed on the upstream-side surface 153 of the third portion 143 and the upstream-side surface 151 of the first portion 141 that forms a downstream-side wall of the first channel 110. Of course, the copper material layer 102 may be formed on the upstream-side surface 153 of the third portion 143 and the upstream-side surface 152 of the second portion 142, and may be formed on the upstream-side surfaces 151, 152, and 153 of the first portion 141, the second portion 142, and the third portion 143.

The photocatalyst layer 103 may be disposed on at least a portion of the second surface 160 of the filter frame 101. The photocatalyst layer 103 may be disposed on at least a portion of the second surface 160 of the filter frame 101 by coating, chemical vapor deposition, physical vapor deposition and the like. As described above, the material 130 flows into the filter frame 101 mainly through the first channel 110, the particulate matter in the material 130 is filtered by the third portion 143, and a gas passed through the third portion 143 is discharged through the second channel 120. Accordingly, the photocatalyst layer 103 may be formed on the downstream-side surface 163 of at least the third portion 143 of the second surface 160. Because a gas may flow into the second channel 120 through the second portion 142, the photocatalyst layer 103 may be formed on the downstream-side surface 163 of the third portion 143 and the downstream-side surface 162 of the second portion 142 that forms an upstream-side wall of the second channel 120. Of course, the photocatalyst layer 103 may be disposed on the downstream-side surface 163 of the third portion 143 and the downstream-side surface 161 of the first portion 141, and may be disposed on the downstream-side surfaces 161, 162, and 163 of the first portion 141, the second portion 142, and the third portion 143.

The photocatalytic layer 103 may include a metal compound capable of causing a photocatalytic reaction by receiving light energy. The metal compound may be, for example, a photocatalyst or photo-activated material having semiconductor characteristics such as $TiO_2$, $WO_3$, or a combination thereof. Light energy may include ultraviolet energy or visible energy. The gas component included in the material 130 passes through the filter frame 101 and comes into contact with the photocatalyst layer 103. The gas component may be decomposed by causing a catalytic reaction while passing through the photocatalyst layer 103, e.g., by reacting with oxygen when the photocatalyst layer 103 is exposed to light energy. The gas component may be a volatile organic compounds (VOC) or other harmful compounds. The volatile organic compound may be, for example, formaldehyde, acetaldehyde, ammonia, toluene, or acetic acid. Bio-particles that have passed through the filter frame 101 without being removed by the copper material layer 102 may be additionally removed from the photocatalytic layer 103 by a photocatalytic action. Accordingly, the removal performance of bio-particles may be improved.

Figure 3:
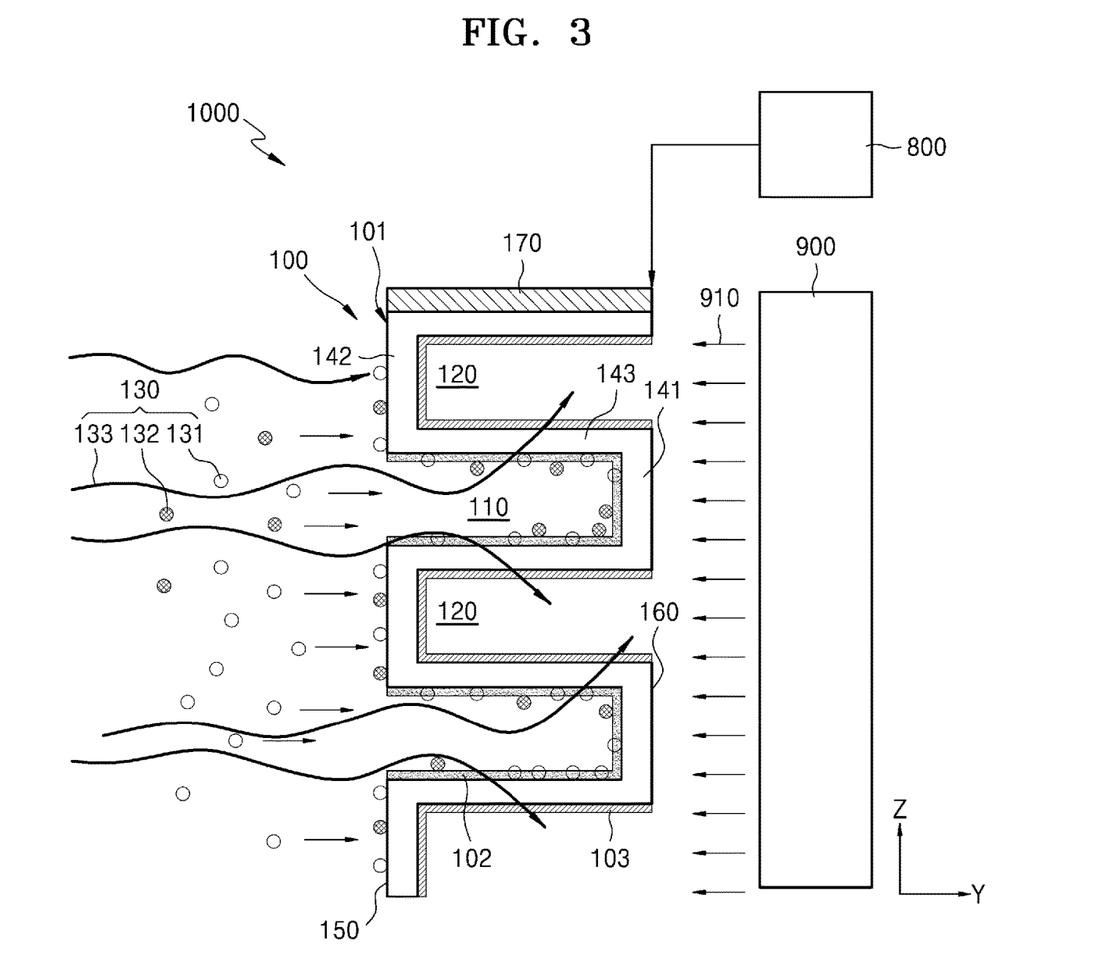
FIG. 3 is a schematic diagram of a filtering system employing the filter shown in FIG. 1, according to an embodiment.

FIG. 3 shows a filtering system 1000 including a filter 100 according to an embodiment. Referring to FIG. 3, the filtering system 1000 includes the filter 100 shown in FIGS. 1 and 2 and a light source 900. The light source 900 generates light energy that activates the photocatalytic layer 103 disposed on the second surface 160 of the filter 100. The light source 900 may irradiate the photocatalytic layer 103 with light energy 910, for example, with ultraviolet energy. The material 130 may include a particulate matter 131, a biomaterial 132, and a gaseous material 133. The particulate matter 131 may be, for example, particles having a diameter of 10 micrometers (μm) or less, that is, fine particles of PM10 or less. The fine particles may include, for example, fine dust. The biomaterial 132 may include, for example, viruses, bacteria, and the like. The gaseous material 133 may include, for example, the volatile organic compound (VOC) described above.

The particulate matter 131 does not pass through the filter frame 101 and accumulates on the first surface 150. Accordingly, the particulate matter 131, such as fine dust may be filtered out from the material 130. The biomaterial 132 is removed by an oligodynamic action of the copper material layer 102 provided on the first surface 150. The gaseous material 133 passing through the filter frame 101 is decomposed by a photocatalytic action of the photocatalytic layer 103 provided on the second surface 160. For example, when the gaseous material 133 includes formaldehyde (HCHO), the formaldehyde causes a catalytic reaction with oxygen present in the second channel 120 while passing through the photocatalytic layer 103, and may be decomposed into water and carbon dioxide ($CO_2$). Therefore, the hazardous gas may be removed. The biomaterial 132 that has passed through the filter frame 101 without being removed by the copper material layer 102 may be additionally removed by the photocatalytic action of the photocatalytic layer 103. In addition, the biomaterial 132 may be additionally removed by a light sterilization action of ultraviolet (UV) light from the light source 900. The light source 900 may irradiate short-wavelength ultraviolet light and provide strong sterilizing power to the photocatalyst layer 103. Accordingly, the removal performance of biomaterials may be improved. As shown in FIGS. 1 and 2, when the filter frame 101 has the plurality of first channels 110 and the plurality of second channels 120 alternately arranged two-dimensionally, areas of the first surface 150 and the second surface 160 are expanded and wide areas of the copper material layer 102 and the photocatalyst layer 103 may be present, and thus, the removal performance of particulate matter, biomaterials, and gaseous materials may be improved.

The filter frame 101 may include a catalyst material that is activated by energy different from light energy. The catalytic material may include a material that is activated by energy different from light energy and causes a catalytic reaction with respect to a gas component included in the material 130. As an example, the filter frame 101 may include a catalyst material that is activated by electrical energy. In this case, the catalyst material may include a metal compound capable of causing an electrically conductive oxygen reduction reaction (ORR). The metal compound may include a compound including a metal, such as Co, Ni, or Mn, or may include a noble metal oxide. As an example, the filter frame 101 may include a catalyst material that is activated by thermal energy. In this case, the catalyst material may include a metal compound capable of causing a low temperature oxidation reaction. The metal compound may include a compound including, for example, Cu, Co, Ni, Fe, Al, Si, or a noble metal. The low temperature oxidation reaction may be an oxidation reaction that occurs between room temperature and 100° C. Thermal energy may include, for example, infrared energy, and may include energy supplied from a heat source, such as a heater.

The third portion 143 of the filter frame 101 may include a catalyst material that is activated by energy other than the light energy described above. Of course, all of the first portion 141, the second portion 142, and the third portion 143 of the filter frame 101 may include a catalyst material that is activated by energy other than the light energy described above. With such a configuration, the removal performance of harmful gas may be improved.

In this case, referring to FIG. 3, the filtering system 1000 may include an external energy source 800. The filter frame 101 may be provided with an energy receiving unit 170 connected to the external energy source 800. The external energy source 800 supplies energy other than light energy to the filter frame 101. In one embodiment, when the filter frame 101 includes a catalyst material that is activated by electrical energy, the energy receiving unit 170 may be an anode electrode, and the filter frame 101 may function as a cathode electrode. The external energy source 800 may supply a current to the filter frame 101 through the energy receiving unit 170. In one embodiment, when the filter frame 101 includes a catalyst material activated by thermal energy, the energy receiving unit 170 may be a heating member. The heating member may convert energy supplied from the external energy source 800, for example, electrical energy into thermal energy, and supply the thermal energy to the filter frame 101.

Figure 4:
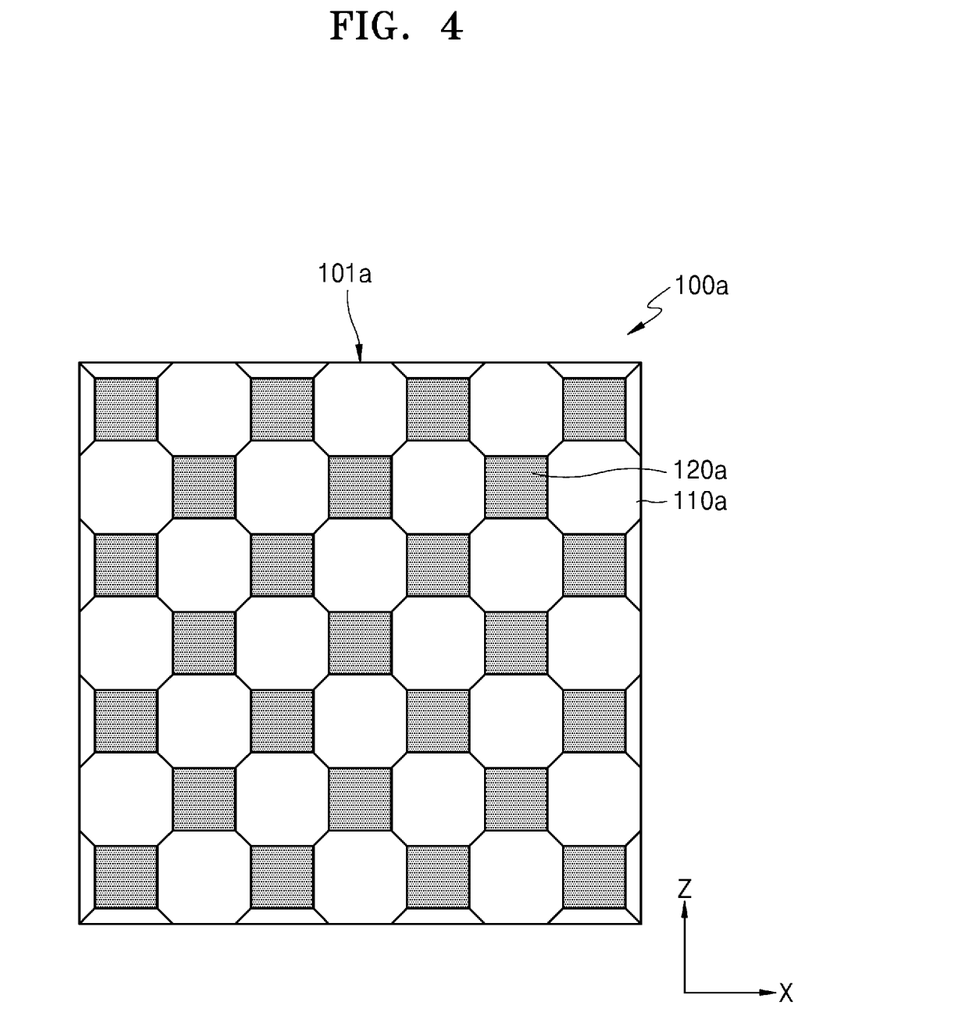
FIG. 4 is a front view of a filter according to an embodiment.
Figure 5:
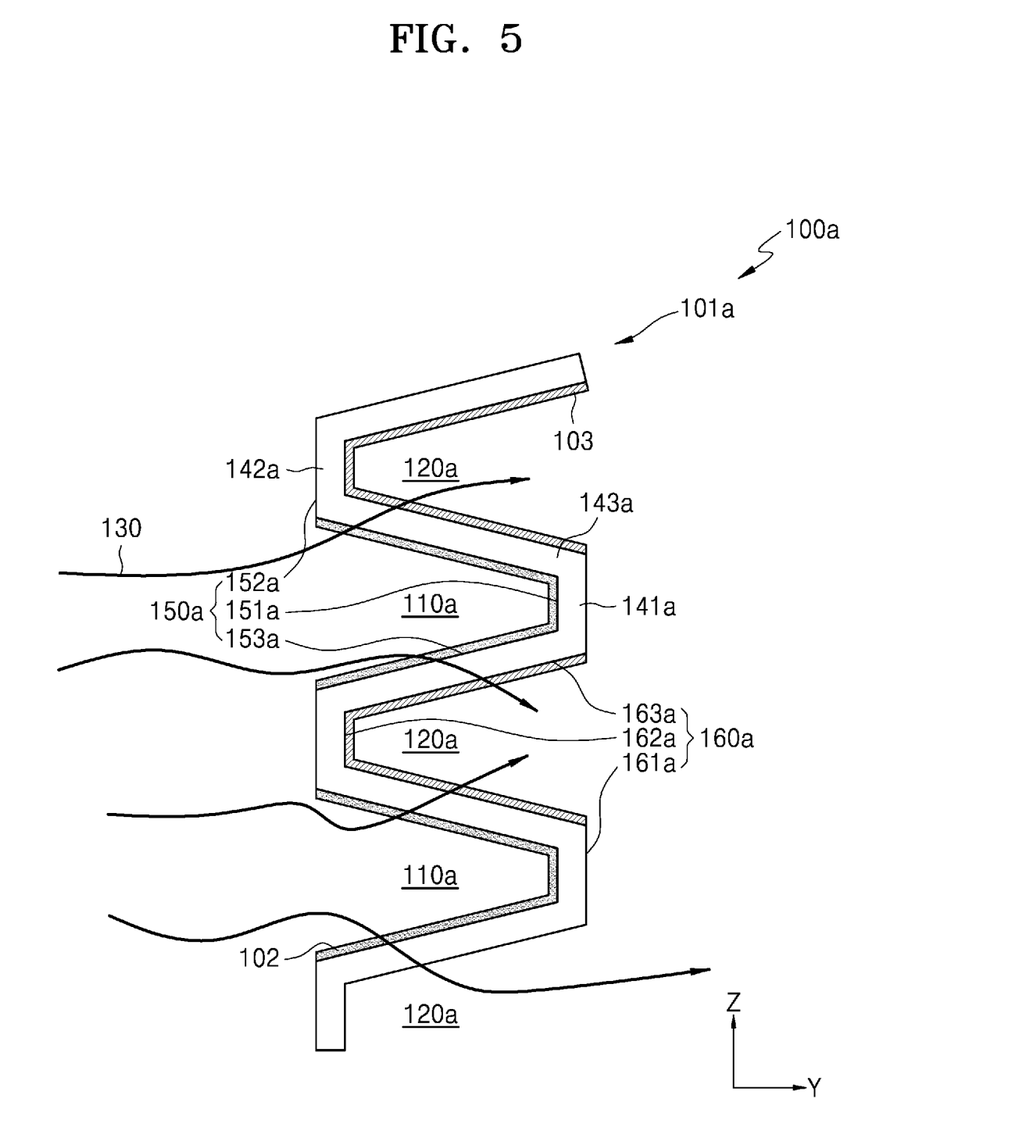
FIG. 5 is a cross-sectional view of the filter shown in FIG. 4, according to an embodiment.

FIG. 4 is a front view of a filter 100*a* according to another embodiment, and FIG. 5 is a cross-sectional view of the filter 100*a* shown in FIG. 4. Referring to FIGS. 4 and 5, the filter 100*a* may include a filter frame 101*a*, a copper material layer 102, and a photocatalyst layer 103. The filter frame 101*a* according to the present embodiment is different from the filter frame 101 shown in FIGS. 1 and 2 in that the filter frame 101*a* includes a plurality of first channels 110*a* having a cross-sectional area gradually reducing toward a thickness direction Y and a plurality of second channels 120*a* having a cross-sectional area gradually increasing toward the thickness direction Y. Accordingly, the above descriptions of the filter 100 and the filter frame 101 may be applied to the filter 100*a* and the filter frame 101*a* as it is.

The filter frame 101*a* may include a first portion 141*a* closing a downstream-side of the first channel 110*a*, a second portion 142*a* closing an upstream-side of the second channel 120*a*, and a third portion 143*a* forming a third between the first channel 110*a* and the second channel 120*a*. The first portion 141*a* and the second portion 142*a* are separated from each other in the thickness direction Y, and the third portion 143*a* may extend obliquely in the Y direction from an edge of the first portion 141*a* and may be connected to the second portion 142*a*. Upstream-side surfaces 151*a*, 152*a*, and 153*a* of the first portion 141*a*, the second portion 142*a*, and the third portion 143*a* become a first surface 150*a*, and downstream-side surfaces 161*a*, 162*a*, and 163*a* of the first portion 141*a*, the second portion 142*a*, and the third portion 143*a* become a second surface 160*a*.

The copper material layer 102 may be disposed on at least a portion of the first surface 150*a* of the filter frame 101*a*. The copper material layer 102 may be disposed on the upstream-side surface 153*a* of at least the third portion 143*a* of the first surface 150*a*. The copper material layer 102 may also be disposed on the upstream-side surface 151*a* of the first portion 141*a* forming a downstream-side wall of the first channel 110*a*. Of course, the copper material layer 102 may also be disposed on the upstream-side surface 152*a* of the second portion 142*a*. The photocatalyst layer 103 may be provided on at least a portion of the second surface 160*a* of the filter frame 101*a*. The photocatalytic layer 103 may be formed on the downstream-side surface 163*a* of at least the third portion 143*a* of the second surface 160*a*. The photocatalyst layer 103 may also be formed on the downstream-side surface 162*a* of the second portion 142*a* forming an upstream-side wall of the second channel 120*a*. Of course, the photocatalyst layer 103 may also be formed on the downstream-side surface 161*a* of the first portion 141*a*.

Figure 6:
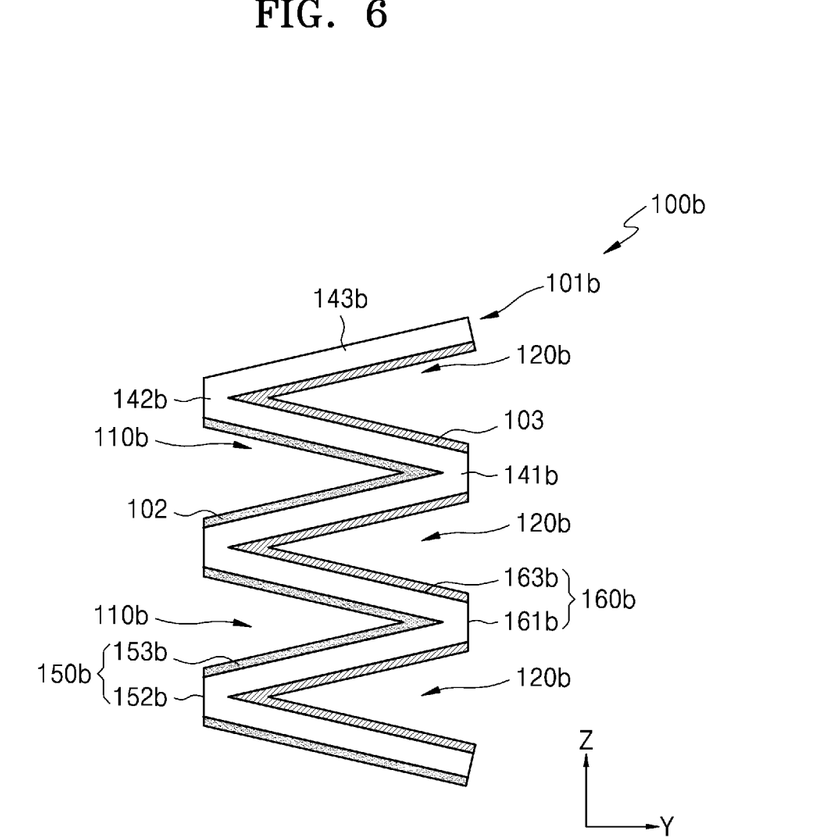
FIG. 6 is a cross-sectional view of a filter according to an embodiment.

FIG. 6 is a cross-sectional view of a filter 100*b* according to another embodiment. Referring to FIG. 6, the filter 100*b* may include a filter frame 101*b*, a copper material layer 102, and a photocatalyst layer 103. The filter frame 101*b* according to the present embodiment is different from the filter frame 101 shown in FIGS. 1 and 2 in that the filter frame 101*b* includes a plurality of wedge-shaped first channels 110*b* having a cross-sectional area gradually reducing toward a thickness direction Y, and a plurality of wedge-shaped second channels 120*b* having a cross-sectional area gradually reducing in a direction opposite to the thickness direction Y. Accordingly, the above description of the filter 100 and the filter frame 101 may be applied to the filter 100*b* and the filter frame 101*b* as it is. The filter frame 101*b* may include a first portion 141*b* closing a downstream-side of the wedge-shaped first channels 110*b*, a second portion 142*b* closing an upstream-side of the wedge-shaped second channels 120*b*, and a third portion 143*b* disposed between the wedge-shaped first channels 110*b* and the wedge-shaped second channels 120*b*. Because the first channels 110*b* and the second channels 120*b* have a wedge-shape, an upstream-side surface of the first portion 141*b* and a downstream-side surface of the second portion 142*b* are not formed. Accordingly, upstream-side surfaces 152*b* and 153*b* of the second portion 142*b* and the third portion 143*b* become a first surface 150*b*, and downstream-side surfaces 161*a* and 163*a* of the first portion 141*b* and the third portion 143*b* become a second surface 160*b*. The copper material layer 102 may be disposed on a portion of the first surface 150*b* of the filter frame 101*b*. The copper material layer 102 may be disposed on the upstream-side surface 153*b* of at least the third portion 143*b* of the first surface 150*b*. The photocatalyst layer 103 may be disposed on a portion of the second surface 160*b* of the filter frame 101*b*. The photocatalyst layer 103 may be disposed on the downstream-side surface 163*b* of at least the third portion 143*b* of the second surface 160*b*.

Figure 7:
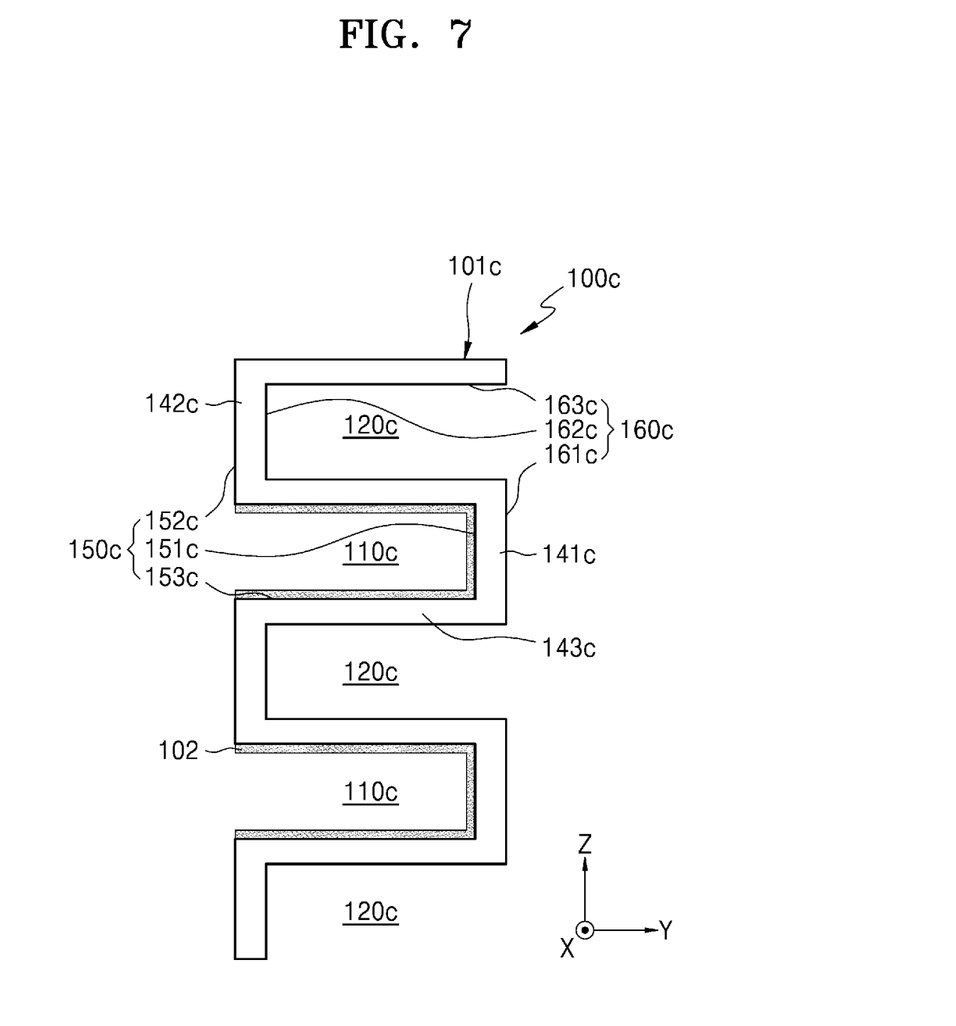
FIG. 7 is a cross-sectional view of a filter according to an embodiment.

FIG. 7 is a cross-sectional view of a filter 101*c* according to another embodiment. Referring to FIG. 7, the filter 100*c* may include a filter frame 101*c* including a photocatalytic material activated by light energy, and a copper material layer 102. The filter frame 101*c* according to the present embodiment is different from the filter frame 101 shown in FIGS. 1 and 2 in that the filter frame 101*c* includes a photocatalytic material activated by light energy. The filter frame 101*c* may be formed of a photocatalyst material itself, and may include a material in which the porous ceramic material and the photocatalyst material described above are mixed. The photocatalytic material may include a metal compound capable of causing a photocatalytic reaction by receiving light energy. The metal compound may be, for example, a photocatalyst material having semiconductor characteristics by light, such as $TiO_2$, $WO_3$, or a combination thereof. Light energy may include ultraviolet energy or visible energy.

The filter frame 101*c* may have, as a whole, the same shape as the filter frame 101 shown in FIG. 2. For example, the filter frame 101*c* may have a shape in which a plurality of first channels 110*c* and a plurality of second channels 120*c* are regularly or irregularly arranged. The plurality of first channels 110*c* and the plurality of second channels 120*c* may be alternately arranged in a two-dimensional arrangement in a direction orthogonal to a thickness direction Y, for example, in the X-direction and Z-direction. The filter frame 101*c* may include a first portion 141*c* closing a downstream-side of the first channel 110*c*, a second portion 142*c* closing an upstream-side of the second channel 120*c*, and a third portion 143*c* disposed between the first channel 110*c* and the second channel 120*c*. Upstream-side surfaces 151*c*, 152*c*, and 153*c* of the first portion 141*c*, the second portion 142*c*, and the third portion 143*c* become a first surface 150, and downstream-side surfaces 161*c*, 162*c*, and 163*c* of the first portion 141*c*, the second portion 142*c*, and the third portion 143*c* become a second surface 160*c*.

A copper material layer 102 may be provided on at least a portion of the first surface 150*c* of the filter frame 101*c*. The copper material layer 102 may be disposed on the upstream-side surface 153*c* of at least the third portion 143*c* of the first surface 150*c*. The copper material layer 102 may also be disposed on the upstream-side surface 151*c* of the first portion 141*c* forming a downstream-side wall of the first channel 110c. Of course, the copper material layer 102 may be disposed on the upstream-side surface 152C of the second portion 142C.

Figure 8:
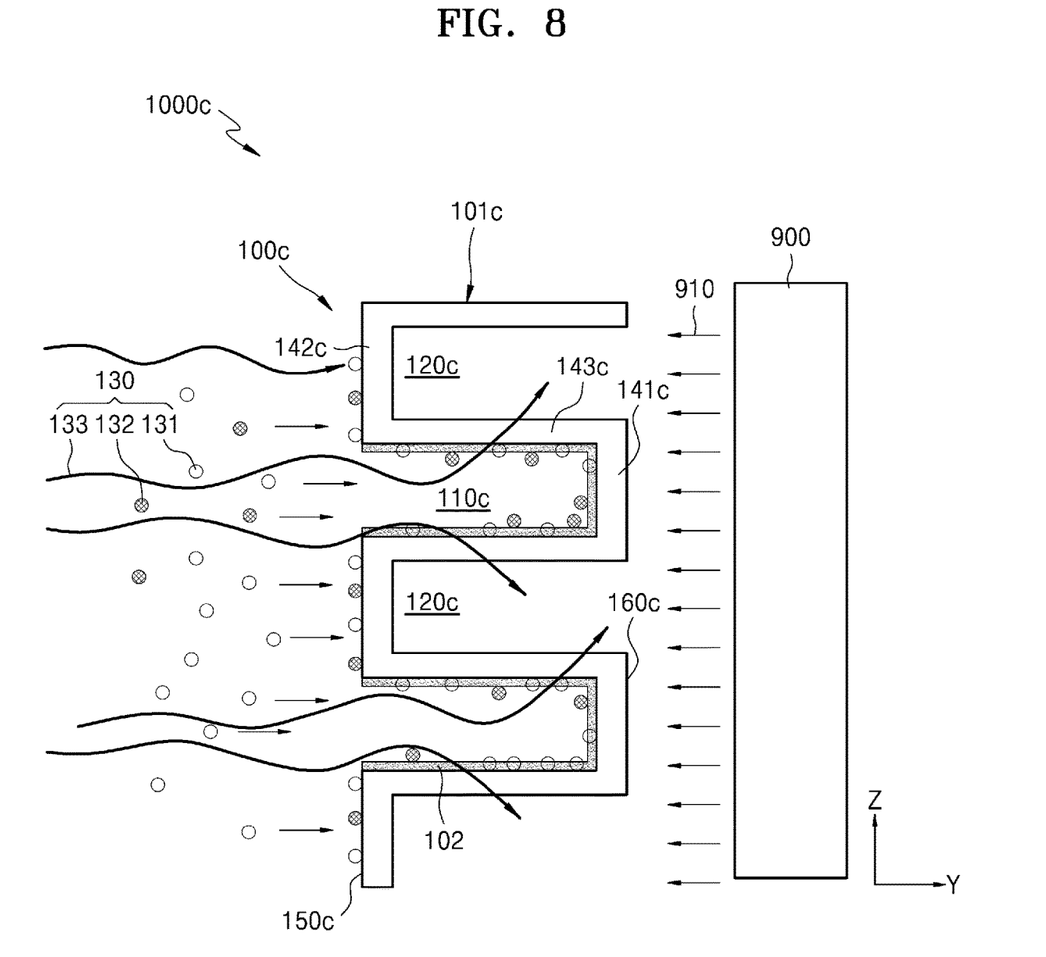
FIG. 8 is a schematic diagram of a filtering system employing the filter shown in FIG. 7, according to an embodiment.

FIG. 8 shows a reproducible filtering system 1000c including the filter 100c according to another embodiment. Referring to FIG. 8, the filtering system 1000c includes the filter 100c shown in FIG. 7 and a light source 900. The light source 900 irradiates the second surface 160c of the filter frame 101c with light energy 910 to activate a photocatalytic material. The light source 900 irradiates the second surface 160c of the filter frame 101c, for example, with ultraviolet light. Ultraviolet light may be, for example, a short wavelength having a strong sterilization action. Accordingly, the photocatalyst layer is activated on the second surface 160c of the filter frame 101c upon exposure to the ultraviolet light.

The material 130 may include a particulate matter 131, a biomaterial 132, and a gaseous material 133. The particulate matter 131 does not pass through the filter frame 101c and accumulates on the first surface 150c. Accordingly, the particulate matter 131, such as fine dust may be filtered out from the material 130. The biomaterial 132 is removed by the oligodynamic action of the copper material layer 102 disposed on the first surface 150c. The gaseous material 133 passing through the filter frame 101c is decomposed by the photocatalytic action of the filter frame 101c. Thereby, harmful gases may be removed. The biomaterial 132 that has passed through the filter frame 101 without being removed by the copper material layer 102 may be additionally removed by the photocatalytic action of the filter frame 101c. In addition, the biomaterial 132 may be additionally removed by a light sterilization action of ultraviolet light irradiating from the light source 900. Accordingly, the removal performance of biomaterials may be improved.

Although not shown in the drawing, instead of the filter frame 101c, a filter frame having a cross-sectional area changes in the thickness direction Y as illustrated in FIG. 5 may be applied. Although not shown in the drawing, instead of the filter frame 101c, various types of filter frames, such as the filter frame 101b having a wedge-shaped cross-sectional area that is changes in the thickness direction Y as shown in FIG. 6, may be used.

Figure 9:
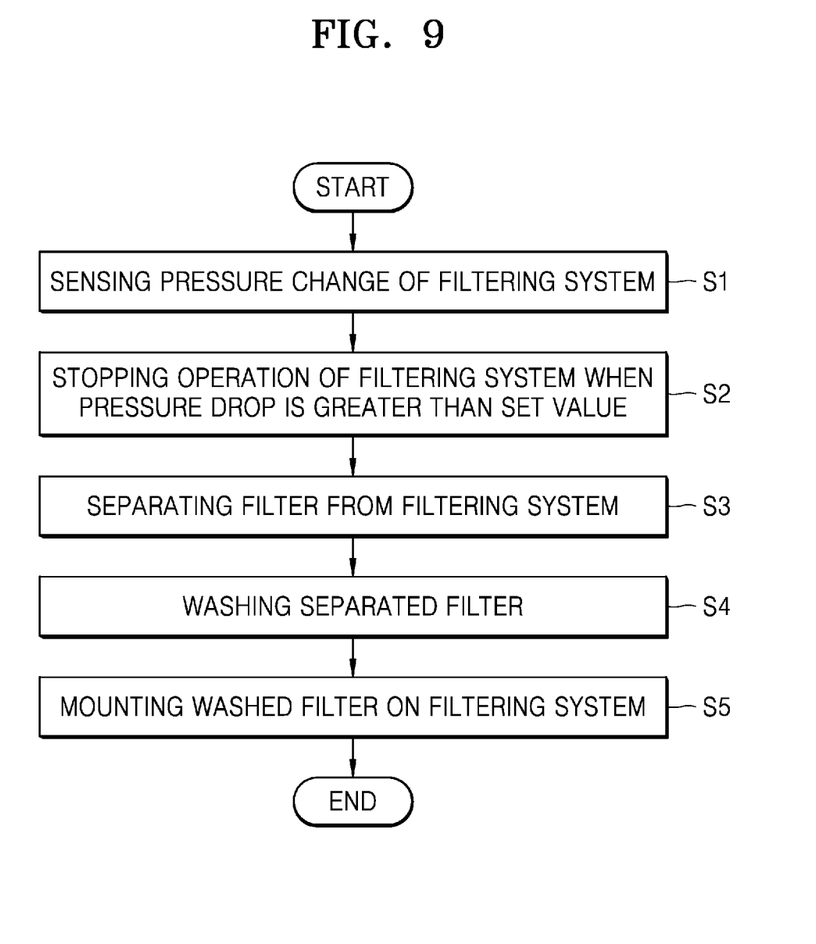
FIG. 9 is a flowchart illustrating a method of managing a filter system including a filter according to an embodiment.

A method of managing a filter system including a filter according to an embodiment will be described. FIG. 9 is a flowchart illustrating a method of managing a filter system according to an embodiment. Referring to FIG. 9, a pressure change in the filter system is sensed (S1). The filter system may include any one of the filter systems shown in FIG. 3 or FIG. 8. After a pressure change is sensed, for example, when the pressure drop is greater than a set value, the operation of the filter system is stopped (S2). In this case, the stop operation may include stopping the entire operation by turning off power of the filter system, or maintain a basic preliminary operation (e.g., a simple blowing operation) of the filter system and stopping only the filtering operation. In addition, the pressure drop may denote a pressure drop on a side of the ceramic catalyst filter through which air is discharged. Sensing a pressure change may be sensing a pressure difference between an air inlet-end and an air outlet-end of the filter. Based on a pressure difference, when the pressure difference is greater than a reference value, for example, 350 Pascal (Pa) or greater, the operation of the filter system may be stopped or maintained as described.

After stopping the filter system, the filter is separated from the filter system (S3). Thereafter, the separated filter is washed (S4). When particulate matter accumulates to an amount that is more than a reference amount on a channel of the air inlet-end of the filter, for example, side and bottom surfaces of the first channel 110 of FIG. 2, a pressure drop is sensed or a pressure difference may increase above a reference value. Therefore, in a washing operation (S4), the separated filter is washed with water or another predetermined solvent or solution to remove layered particulate material that has accumulated on the filter.

After washing the filter in this way, the washed filter is mounted back on the filter system (S5).

The filter frame of the disclosed filter forms a porous monolithic frame or a monolithic structure. Therefore, the disclosed filter does not require an additional support. Also, the porous filter frame filters out particulate matter from incoming material, and the copper material layer removes bio-particles by an oligodynamic action. Gaseous materials passing through the filter frame is decomposed by a photocatalytic reaction of a photocatalytic layer or a photocatalytic material. Accordingly, the disclosed filter may simultaneously remove particulate matter, biomaterials including viruses or bacteria, and gaseous materials.

Because the disclosed filter may be repeatedly reused, consumption cost may be reduced and resource waste may also be reduced. Also, because the filter may be reused simply by washing with a solvent or solution, such as water, maintenance management is relatively straight-forward.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A filter comprising:
   a porous filter frame having a first upstream-side surface, and a second downstream-side surface based on a thickness direction, the porous filter frame filtering particulate matter; and
   a copper material layer disposed on at least a portion of the first upstream-side surface,
   wherein
   the filter frame includes a plurality of first channels extending in the thickness direction, the first channels having an open upstream-side and a closed downstream-side, and a plurality of second channels extending in the thickness direction and having an open downstream-side and a closed upstream-side, and
   a first portion that closes the downstream-side of the plurality of first channels, a second portion that closes the upstream-side of the plurality of second channel, and a third portion disposed between the first channel and the second channel,
   wherein the permeability of the first portion and the second portion to the particulate matter is less than the third portion.

2. The filter of claim 1, wherein the copper material layer comprises copper(0), copper(I), or a combination thereof.

3. The filter of claim 2, wherein the copper material layer is disposed on a first surface of the third portion.

4. The filter of claim 3, wherein the copper material layer is disposed on a first surface of the second portion.

5. The filter of claim 1, further comprising a photocatalyst layer that is disposed on the second downstream-side surface, wherein the photocatalyst layer is activated by light energy.

6. The filter of claim 5, wherein the photocatalyst layer includes a metal compound that has a semiconductor characteristic in response to light exposure, and the metal compound includes $TiO_2$, $WO_3$, or a combination thereof.

7. The filter of claim 5, wherein the filter frame comprises a catalyst material that is activated by energy other than light to remove gaseous materials.

8. The filter of claim 1, wherein the filter frame comprises a photocatalyst material that is activated by light energy.

9. The filter of claim 1, wherein
the plurality of first channels and the plurality of second channels are alternately arranged in a two-dimensional arrangement in a plane orthogonal to the thickness direction.

10. The filter of claim 1, further comprising a photocatalytic layer that is disposed on a second surface of the third portion, wherein the photocatalytic layer is activated by light energy.

11. The filter of claim 10, wherein the photocatalyst layer is disposed on a second surface of the first portion.

12. The filter of claim 10, wherein the filter frame comprises a catalyst material that is activated by energy other than light energy to remove a gaseous materials.

13. The filter of claim 1, wherein the filter frame comprises a photocatalyst material that is activated by light energy.

14. A filter system comprising:
a filter, the filter including a porous filter frame having a first upstream-side surface, and a second downstream-side surface based on a thickness direction, the porous filter frame filtering particulate matter, and a copper material layer disposed on at least a portion of the first upstream-side surface;
wherein the filter frame includes a plurality of first channels extending in a first direction, the first channels having an open upstream-side and a closed downstream side, and a plurality of second channels extending in the first direction and having an open downstream-side and a closed upstream-side; and
the filter frame includes a first portion that closes the downstream-side of the first channel, a second portion that closes the upstream-side of the second channel, and a third portion disposed between the first channel and the second channel, and the copper material layer is disposed on a first surface of the third portion,
wherein the permeability of the first portion and the second portion to the particulate matter is less than the third portion; and
a light source configured to irradiate the second downstream-side surface of the filter frame.

15. The filter system of claim 14, further comprising a photocatalytic layer that is disposed on the second downstream-side surface, wherein the photocatalytic layer is activated by the light irradiated from the light source.

16. The filter system of claim 15, wherein the filter frame comprises a catalyst material that is activated by energy other than light energy.

17. The filter system of claim 14, wherein the filter frame comprises a photocatalyst material that is activated by the light irradiated from the light source.

18. The filter system of claim 14, wherein
the plurality of first channels and the plurality of second channels are alternately arranged in a two-dimensional arrangement in a plane orthogonal to the first direction.

* * * * *